United States Patent [19]

Becker et al.

[11] Patent Number: 5,717,098

[45] Date of Patent: Feb. 10, 1998

[54] PROCESS FOR THE PREPARATION OF AZANORADAMANTANE BENZAMIDES

[75] Inventors: Daniel Paul Becker, Glenview; Daniel Lee Flynn, Mundelein; Alan Edward Moormann, Skokie; Clara Ines Villamil, Glenview, all of Ill.

[73] Assignee: G. D. Searle & Co., Chicago, Ill.

[21] Appl. No.: 681,139

[22] Filed: Jul. 22, 1996

Related U.S. Application Data

[63] Continuation of Ser. No. 269,412, Jun. 30, 1994, abandoned.

[51] Int. Cl.$^6$ .............. C07D 221/06; C07D 221/18; C07D 451/14; C07D 307/93
[52] U.S. Cl. .............. 546/75; 546/74; 546/94; 546/97; 546/98; 549/304; 549/305; 549/311
[58] Field of Search .............. 546/74, 75, 94, 546/97, 98; 549/304, 305, 311

[56] References Cited

U.S. PATENT DOCUMENTS

| | | | |
|---|---|---|---|
| 5,140,023 | 8/1992 | Becker et al. | 514/214 |
| 5,223,613 | 6/1993 | Becker et al. | 540/586 |

OTHER PUBLICATIONS

Daniel L. Flynn, et al. "New Aza(Nor) Adamantanes are Agonists at the Newly Identified Serotonin 5-HT4 Receptor and Antagonists at the 5-HT3 Receptor", *Bioorganic & Medicinal Chemistry Letters*, vol. 2, No. 12, pp. 1613-1618, 1992.

Günter Helmchen, et al. "Building Blocks for the Synthesis of Enantiomerically Pure Jasmonoids: Synthesis of (+)-Methyl Epijasmonate**", *Angew. Chem. Int. Ed. Engl. 29*, (1990) No. 9, pp. 1024-1025.

Horst Hartmann, et al. "High Stereoselectivity in Lewis-Acid-Catalyzed and Uncatalyzed Diels-Alder Reactions of the Fumarate of (S) Ethyl Lactate**", *Angew. Chem. Int. Ed. Engl. 26*, (1987), No. 11, pp. 1143-1145.

Günter Helmchen, et al. "Asymmetric Diels-Alder Reactions with Chiral Enoates as Dienophiles", *Modern Synthetic Methods, 1986*, vol. 4, pp. 263-306.

D. L. Flynn et al. Use of Atom-Transfer Radical Cyclizations as an Efficient Entry into a New "Serotonergic" Azanoradamantane, *Tetrahedron Letters*, vol. 33, No. 48, 1992, Oxford GB, pp. 7283-7286.

J. Neumeister et al. Ozone Cleavage of Olefins with Formation of Ester Fragments, *Angewandte Chemie International Edition,*, vol. 17, No. 12, 1978 Weinheim De, pp. 939-940.

Abstract—Database WPI, *Derwent Publications Ltd.*, London, GB; AN 92-069451 and JP, A, 04 013 663 (Sumitomo Seiyaku KK), Jan. 17, 1992.

*Primary Examiner*—Ba K. Trinh
*Attorney, Agent, or Firm*—Cynthia S. Kovacevic; Roger A. Williams

[57] ABSTRACT

A process for the preparation of a γ-lactone of the formula

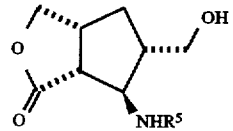

which can be used to produce a single enantiomer of aminoazanoradamantane which is coupled to aromatic acid moieties to produce compounds useful as 5-HT agonists or antagonists.

13 Claims, No Drawings

PROCESS FOR THE PREPARATION OF AZANORADAMANTANE BENZAMIDES

This is a continuation of U.S. Ser. No. 08/269,412 filed Jun. 30, 1994 now abandoned.

BACKGROUND OF THE INVENTION

The invention herein is directed to a process for the preparation of a γ-lactone of the formula

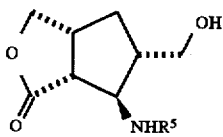

wherein $R^5$ is a protecting group selected from the group consisting of tosyl, pivaloyl or trityl. Such compounds are useful in the preparation of a single enantiomer of amino azanoradamantane.

The invention herein is further directed to a process for the preparation of compounds of the general formula

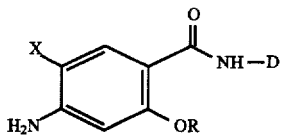

wherein X represents halogen, R represents hydrogen or lower alkyl and D is an azanoradamantane moiety as discussed hereinafter. Such compounds are useful as 5-HT agonists and/or antagonists.

It is disclosed in U.S. Pat. No. 5,140,023 and U.S. Pat. No. 5,223,613 that such azanoradamantane compounds can be prepared by reacting a trans-1,2-dicarbomethoxy-4-methylene-cyclopentane with sodium hydroxide, followed by reaction with an acid to produce trans-4-methylene-1,2-cyclopentane-dicarboxylic acid. The dicarboxylic acid is reacted with acetic anhydride to produce cis-tetrahydro-5-methylene-1H-cyclopenta[c]furan-1,3(3aH)-dione which is reacted with ammonia gas and methylene chloride to produce the ammonium salt. Reaction of the ammonium salt with acetyl chloride produces the amide which is reacted with lithium aluminum hydride and di-5 t-butyl dicarbonate to produce cis-1,1-dimethylethylhexahydro-5-methylene-cyclopenta[c]pyrrole-2(1H)-carboxylate. The product is reacted with bis(p-toluenesulfonyl)-sulfodiimide to produce the p-toluenesulfonamide which is reacted with thexyl borane to produce an endo-alcohol. The endo-alcohol is reacted with p-toluenesulfonyl chloride to produce a tosylate which is reacted with trifluoroacetic acid and treated with Hunig's base to provide the p-toluenesulfonamide azacycle. The azacycle is reductively cleaved to produce the aminoazacycle which is coupled with a benzoic acid derivative under mixed anhydride conditions to give the protected benzamide azacycle. Deprotection by hydrolysis and treatment with hydrochloric acid produces the desired benzamide azacycles.

It would be desirable to provide a process for the production of such benzamide azacycles which process requires fewer steps and is thereby more efficient, is feasible for commercial scale-up and produces a single enantiomer (as opposed to a racemic mixture).

SUMMARY OF THE INVENTION

The invention herein is directed to a process for the preparation of a γ-lactone of the formula

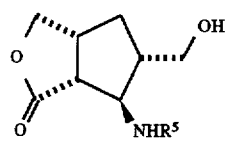

wherein $R^5$ is as described above.

The invention herein is further directed to a process for the preparation of azanoradamantyl benzamides and derivatives thereof.

The invention herein is further more specifically directed to the preparation of azanoradamantanes (D) of the formula

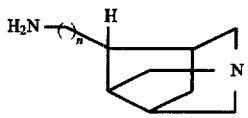

wherein n is 0 or 1 which is used for coupling to an benzoic acid moiety.

More specifically, an embodiment of the present invention is performed by treating an enantomerically enriched iodolactone of the formula:

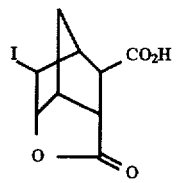

with thionyl chloride to give the corresponding acid chloride which is converted to the primary amide by treatment with ammonia. The primary amide is treated with HTIB [hydroxy (tosyloxy) iodobenzene], followed by tosylation with toluenesulfonyl chloride in pyridine to afford the tosylamine:

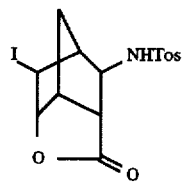

Treatment of the tosylamine with zinc in acetic acid affords the norbornene carboxylic acid:

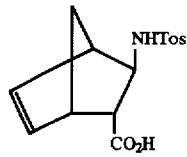

Ozonolysis, followed by treatment with sodium borohydride and an acidic workup, yields the γ-lactone:

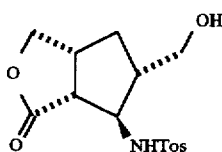

Ammonolysis of the γ-lactone in methanol affords the primary amide diol:

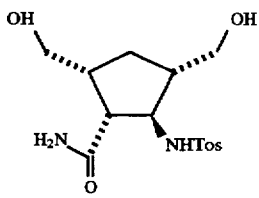

which is reduced with borane to the primary amine and protected as the t-butyl carbamate diol. Tosylation of the protected diol with toluenesulfonyl chloride in pyridine, deprotection of the t-butyl carbamate with trifluoroacetic acid and subsequent treatment with diisopropylethylamine in acetonitrile affords the tosylamino azanoradamantane of the formula:

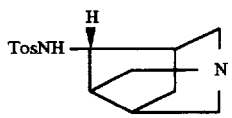

Deprotection of the tosylamino azanoradamantane under Birch conditions (alkali metal/ammonia), affords the desired aminoazanoradamantane. The aminoazanoradamantane can be coupled, directly without separation or purification, to a substituted benzoic acid to yield

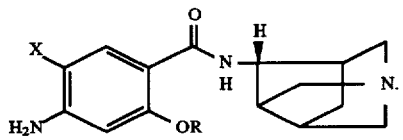

More specifically, the aminoazanoradamantane can be coupled, directly without separation or purification, with 4-amino-5-chloro-2-methoxybenzoic acid in the presence of CDI (1,1'-carbonyldiimidazole) to afford the desired azanoradamantane benzamide enantiomer of the formula:

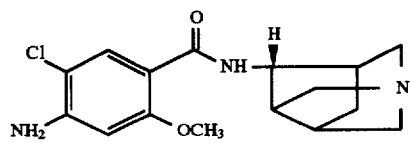

which is isolated directly by crystallization from the reaction mixture.

DETAILED DESCRIPTION OF THE INVENTION

The invention herein is directed to a process for the preparation of a γ-lactone of the formula

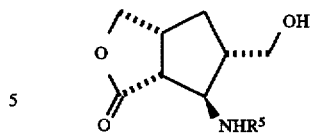

wherein $R^5$ is as described above.

The invention herein is further directed to a process for preparing aminoazanoradamantane compounds and is further directed to the coupling of such aminoazanoradamantane compounds to benzoic acids.

Benefits of using the process, disclosed herein, over previously disclosed preparations include: 1) a more economical and efficient synthesis requiring fewer steps and fewer reagents than known processes; 2) a process amenable to commercial scale-up; and 3) a process for the production of a single enantiomer without resolution and/or purification steps.

The processes of the present invention can be illustrated without limitation by the following reaction Schemes A, I, II, IIA, III and IV.

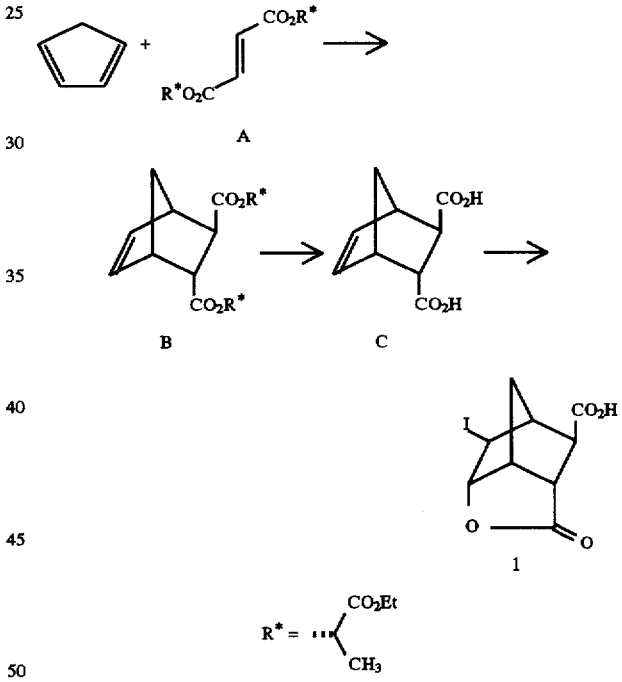

Gunther Helmchen [Angew. Chem. Int. Ed. Engl. 29 (1990) 1024–1025; Angew. Chem. Int. Ed. Engl. 26 (1987) 1143–1145; DE 3702084 Al] has described the synthesis of iodolactone 1 (Scheme A). According to Helmchen, treatment of fumaryl chloride with ethyl-(S)-lactate and a base, such as triethylamine, in a chlorinated hydrocarbon solvent gives bis-ethyl-(S)-fumarate ester A. The present inventors have found that toluene may be successfully substituted for the chlorinated hydrocarbon solvent in the preparation of A. Treatment of A, according to the methodology of Helmchen, with cyclopentadiene in a solvent, preferably a chlorinated hydrocarbon or a mixture of an alkane and a chlorinated hydrocarbon, gives the (2R,3R)-diastereomer B as the predominant product.

The present inventors have found that Helmchen's method gives excellent diastereomeric ratios when performed in carbon tetrachloride/hexane, as reported in Table I. This previously disclosed method, however, is undesirable for large-scale developmental synthesis of B, since chlorinated hydrocarbons are to be avoided, and in particular the hazardous (carcinogenic) solvent carbon tetrachloride is undesirable for developmental-scale syntheses. The other solvents prescribed by Helmchen gave inferior diastereomeric excess (de) as reported in Table I. The present inventors unexpectedly discovered, however, that utilization of environmentally benign triethylamine as the solvent gave the desired diastereomer B in high diastereomeric excess.

The bis-ester B undergoes saponification to C and iodolactonization to 1 according to Helmchen's method [Modern Synthetic Methods 1986, p.261].

TABLE I

| Solvent | Temp | Time | R—S %** |
|---|---|---|---|
| 1:3 CCl₄/Hexane | −25° C. | 2.0 hr | 95.6/4.3 |
| Toluene | 0° C. | 1.0 hr | 82.3/17.6 |
| Toluene | −60→0° C. | 1.0 hr | 83.8/16.2 |
| Heptane | −60→0° C. | 1.0 hr | 83.8/16.2 |
| Heptane | −25° C. | 2.0 hr | 80.4/19.6 |
| 1:3 Et₃N/Heptane | −25° C. | 0.5 hr | 84.2/14.7 |
| 1:3 Pr₃N/Heptane | −25° C. | 0.5 hr | 89.4/10.6 |
| 1:3 MTBE*/Heptane | −25° C. | 0.5 hr | 85.6/14.4 |
| 1:3 CCl₄/Heptane | −25→−14° C. | 0.5 hr | 85.2/14.8 |
| 1:3 CCl₄/Hexane | −25→−14° C. | 0.5 hr | 85.1/14.9 |
| 1:3 CCl₄/Cyclo-Hexane | −25→−14° C. | 0.5 hr | 84.9/15.1 |
| MTBE* | −26→−21° C. | 0.5 hr | 83.3/16.7 |
| i-Octane | −26→−21° C. | 0.5 hr | 85.1/14.9 |
| 1:1 i-Octane/Heptane | −26→−21° C. | 0.5 hr | 89.2/10.8 |
| 1:3 CCl₄/i-Octane | −26→−23° C. | 0.5 hr | 91.9/9.9 |
| 1:3 MTBE/i-Octane | −26→−23° C. | 0.5 hr | 90.4/9.6 |
| Et₃N | −26→−23° C. | 0.5 hr | 96.6/3.4 |

*methyl t-butyl ether
**R—S %: Percentage of 2R,3R/Percentage of 2S,3S as determined by HPLC

SCHEME I

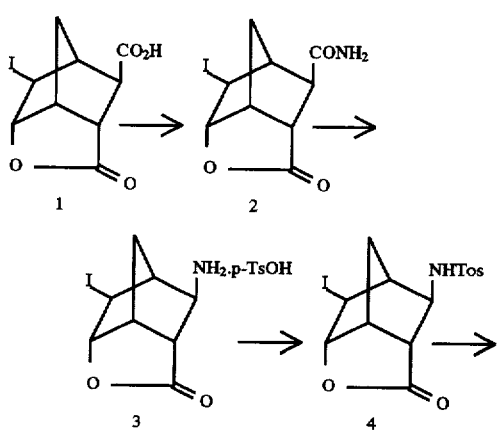

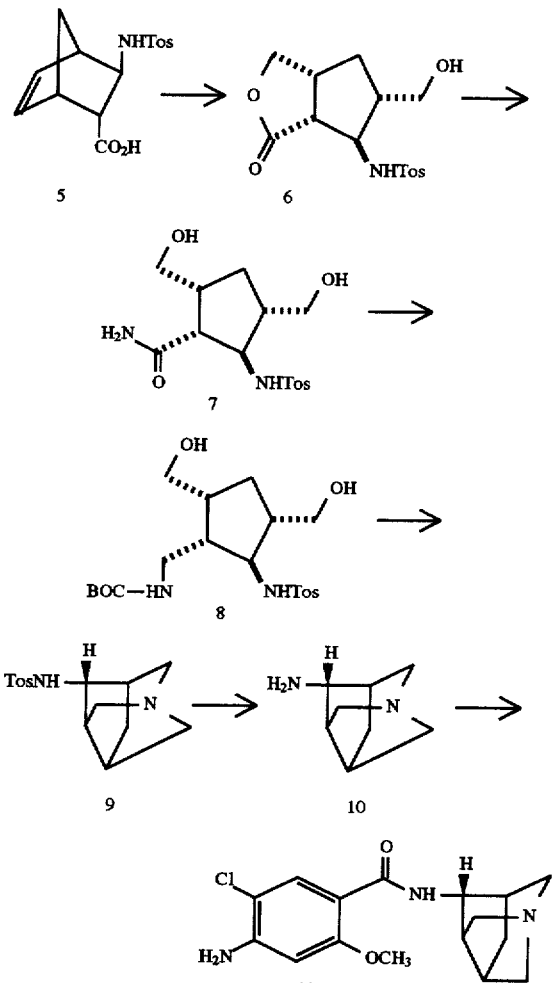

Scheme I describes the preferred enantioselective synthesis of azanoradamantane benzamide 11. Iodolactone 1 is treated with thionyl chloride to give the corresponding acid chloride which is converted to the primary amide 2 by treatment with ammonia. [Racemic 2 was previously prepared by a different route [JP 04013663 (1992); CA 116(25) :255175s] from cis-5-norbornene-endo-2,3-dicarboxylic anhydride.] The primary amide 2 is then treated with HTIB [hydroxy(tosyloxy)iodobenzene] to afford the p-toluenesulfonic acid salt 3, followed by tosylation of the amine with toluenesulfonyl chloride in pyridine to afford the tosylamine 4. Treatment with zinc in acetic acid affords the norbornene carboxylic acid 5. Ozonolysis of 5, followed by treatment with sodium borohydride and an acidic workup yields the gamma-lactone 6. Ammonolysis of the gamma-lactone in methanol, affords the primary amide diol 7, which is reduced with borane to the primary amine and protected as the tert-butyl carbamate diol 8. Tosylation of the diol with toluenesulfonyl chloride in pyridine, deprotection of the tert-butyl carbamate with trifluoroacetic acid, and subsequent treatment with diisopropylethylamine in acetonitrile, affords the tosylaminoazanoradamantane 9. Deprotection of the tosylamine under Birch conditions, with alkali metals, and more preferably with calcium metal, affords the aminoazanoradamantane 10. The aminoazanoradamantane 10 is coupled directly, without resolution or purification, with 4-amino-5-chloro-2-methoxybenzoic acid in the presence of CDI to afford the desired azanoradamantane benzamide (+)-11 enantiomer, which is isolated directly by crystallization from the reaction mixture. The azanoradamantane benzamide 11 is then converted to the monohydrochloride salt. The present conversion of 10 to 11 is advantageous over the previously disclosed (racemic) preparation of 11 from 10 described in U.S. Pat. No. 5,140,023 and U.S. Pat. No. 5,223,613. The previous method involved the coupling of racemic 10 with 4-acetamido-5-chloro-2-methoxybenzoic acid to afford the acetamide-protected derivative of 11. The acetamide-protected derivative was then isolated by chromatography and required a subsequent deprotection step.

-continued
SCHEME IIA

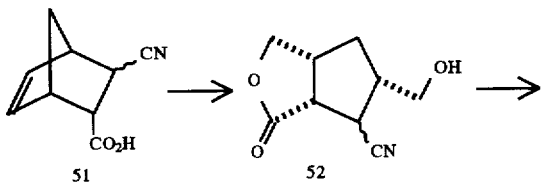

SCHEME II

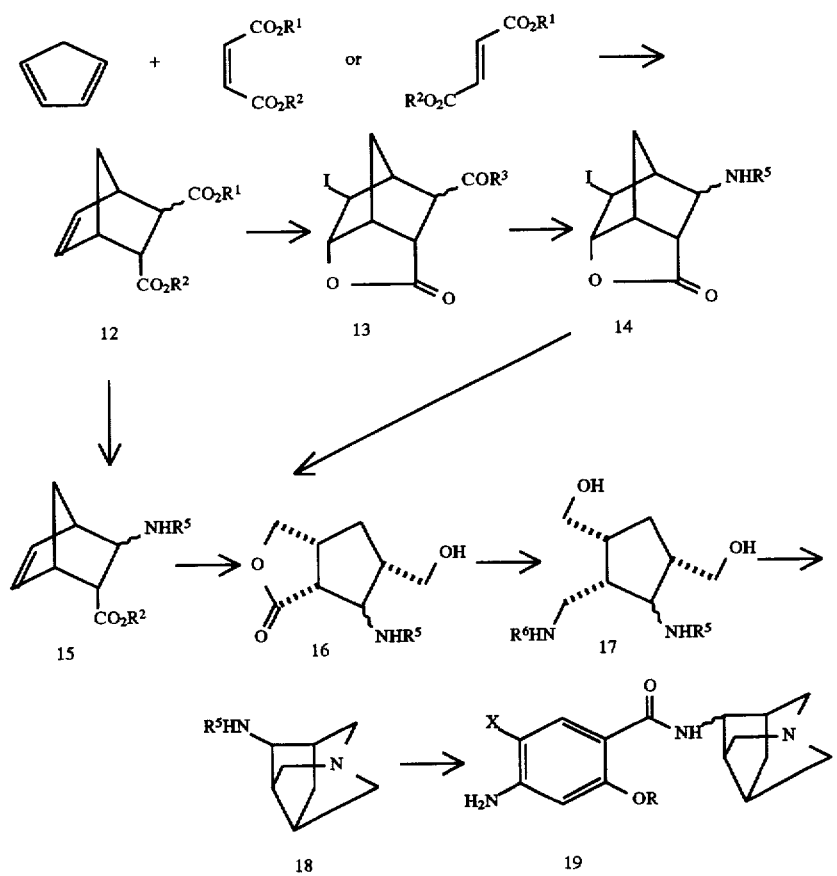

SCHEME IIA

-continued
SCHEME IIA

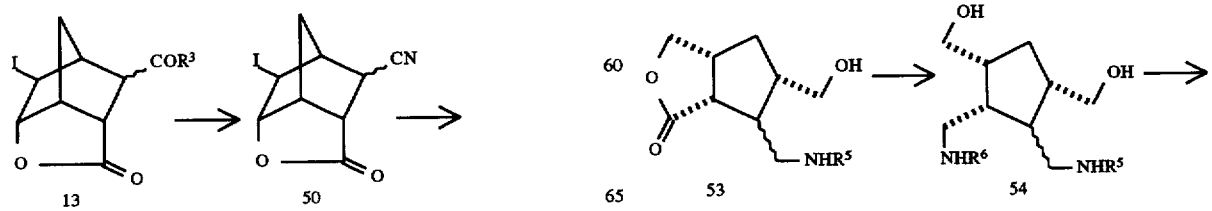

-continued
SCHEME IIA

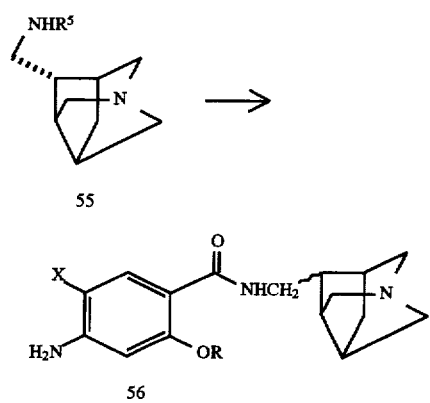

Schemes II and IIa describe alternate embodiments of the present invention. In Scheme II a Diels-Alder reaction between cylopentadiene and a maleic acid mono-or di-ester or a fumaric acid mono- or di-ester affords the bicyclic derivative 12. $R^1$ and $R^2$ are independently H; a metal cation such as Li+, Na+, or K+; (branched) alkyl; chiral auxiliary groups such as lactate, menthol, camphor, 8-phenylmenthol, or 3,3-dimethylbutan-2-ol. The Diels-Alder reaction performed in a variety of solvents including aromatic hydrocarbons such as toluene; hydrocarbons such as hexane, cyclohexane, and heptane; trialkylamines such as triethylamine; chlorinated hydrocarbons such as methylene chloride and chlorobenzene; or water. The Diels-Alder reaction performed without a catalyst or with a Lewis-acid catalyst such as $TiCl_4$, $BF_3$, $AlCl_3$, $EtAlCl_2$, $Et_2AlCl$, $SnCl_4$, or MAD [methylaluminum bis(2,6-di-tert-butyl-4-methylphenoxide], and can also be performed with a chiral Lewis acid catalyst many of which are known. The bicyclic adduct 12 can be resolved as a mono or diester, if necessary, or can be saponified to the diacid ($R^1$, $R^2$=H) for resolution via classical means such as diastereomeric salt formation with a chiral base, such as brucine or a single enantiomer of alpha-methylbenzylamine.

The diacid 12 ($R^1$, $R^2$=H) can be iodolactonized under standard conditions to give the iodolactone carboxylic acid 13 ($R^3$=OH). The carboxylic acid can be rearranged to the amine derivative 14 under classical Curtius, Koser, or Schmidt conditions. For example, conversion of the carboxylic acid to the acid chloride with oxalyl chloride, or a mixed anhydride with isobutylchloroformate, followed by treatment with sodium azide gives an acyl azide which can be thermally rearranged in the presence of an alcohol ($R^4OH$) to give a carbamate derivative 14 ($R^5=CO_{2R}^4$). Alternatively, the carboxylic acid 13 is converted to a primary amide ($R^3=NH_2$) via treatment of the corresponding acid chloride or mixed anhydride with ammonia followed by Koser's reagent (HTIB), with or without added iodobenzene diacetate, giving the corresponding amine 14 ($R^5$=H).

The amine 14 can be directly protected with a variety of protecting groups ($R^5$) such as tosyl, cbz (carboxybenzoyloxy), pivaloyl, trityl, or carbomethoxy. Reductive elimination of the iodolactone with zinc and acetic acid then gives rise to bicyclic derivative 15 ($R^2$=H).

The bicyclic derivative 12 can also be converted directly to the amine derivative 15 when the endo carboxyl is suitably protected ($R^2$=benzyl or methyl, for example) and $R^1$=H, via the Curtius, Koser, or Schmidt conditions described above. Oxidative cleavage of the olefin 15 followed by reduction gives rise to lactone 16, which can be accomplished via ozonolysis followed by treatment with sodium borohydride, or via osmium tetroxide oxidation with sodium periodate followed by sodium borohydride reduction. Ammonolysis of the lactone 16 yields a primary amide which can be reduced with such reagents as borane to give a primary amine. Protection of the primary amine with an appropriate protecting group ($R^6$) such as BOC, trityl, or pivaloyl gives the diol 17. The hydroxyl groups of 17 are converted into leaving groups such as tosylates, trifluoromethanesulfonates, or halides, and the $R^6$ protecting group is removed, for example by treatment with trifluoroacetic acid when $R^6$=BOC (tert-butyloxycarbonyl). Subsequent treatment with base affords the amino azanoradamantane 18. A variety of organic or inorganic bases can be employed for the conversion of 17 to 18, including triethylamine, diisopropylethylamine (Hunig's base), potassium or cesium carbonate, and sodium hydroxide, and the reaction can be carried out in any suitable inert solvent or solvent mixtures including acetonitrile, DMF (dimethylformamide), THF (tetrahydrofuran), toluene, alcohol, or water.

Deprotection of the aminoazanoradamantane 18 is accomplished under appropriate conditions, such as with a dissolving metal reduction employing lithium, sodium, or calcium in THF/liquid ammonia for the tosylate derivative ($R^5$=tosyl) to give the free amine which is coupled under standard conditions, such as in the presence of CDI, with an appropriate 4-aminobenzoic acid derivative to yield the desired benzamide derivative 19.

In Scheme IIA the iodolactone 13 ($R^3=NH^2$) is dehydrated with trifluoroacetic anhydride or toluenesulfonyl chloride in pyridine to afford the nitrile 50. Reductive elimination of the iodolactone with zinc and acetic acid gives rise to norbornene carboxylic acid 51. Oxidative cleavage of 51 followed by reduction gives rise to lactone 52, which can be accomplished via ozonolysis followed by treatment with sodium borohydride, or via osmium tetroxide oxidation with sodium periodate followed by sodium borohydride reduction. Reduction of the nitrile of 52 is accomplished via treatment with hydrogen in the presence of a catalyst, such as Raney nickel or palladium on carbon, followed by protection with an appropriate protecting group, ($R^5$) such as tosyl, by treatment with tosyl chloride in pyridine. Ammonolysis of the lactone 53, yields a primary amide which can be reduced with such reagents as borane to give a primary amine. Protection of the primary amine with an appropriate protecting group ($R^6$) such as BOC, trityl, or, pivaloyl gives the diol 54. The hydroxyl groups of 54 are converted into leaving groups such as tosylates, trifluoromethanesulfonates, or halides, and the $R^6$ protecting group is removed, for example by treatment with trifluoroacetic acid when $R^6$=BOC. Subsequent treatment with base affords the azanoradamantane 55. A variety of organic or inorganic bases can be employed for the conversion of 54 to 55, including triethylamine, diisopropylethylamine (Hunig's base), potassium or cesium carbonate, and sodium hydroxide, and the reaction can be carried out in any suitable inert solvent or solvent mixtures including acetonitrile, DMF, THF, toluene, alcohol, or water. Deprotection of the aminoazanoradamantane 55 is accomplished under appropriate conditions, such as with a dissolving metal reduction employing lithium, sodium, or calcium in THF/liquid ammonia for the tosylate derivative ($R^5$=tosyl), to give the free amine which is coupled under standard conditions, such as in the presence of CDI, with an appropriate 4-aminobenzoic acid derivative to yield the desired benzamide derivative 56.

SCHEME III

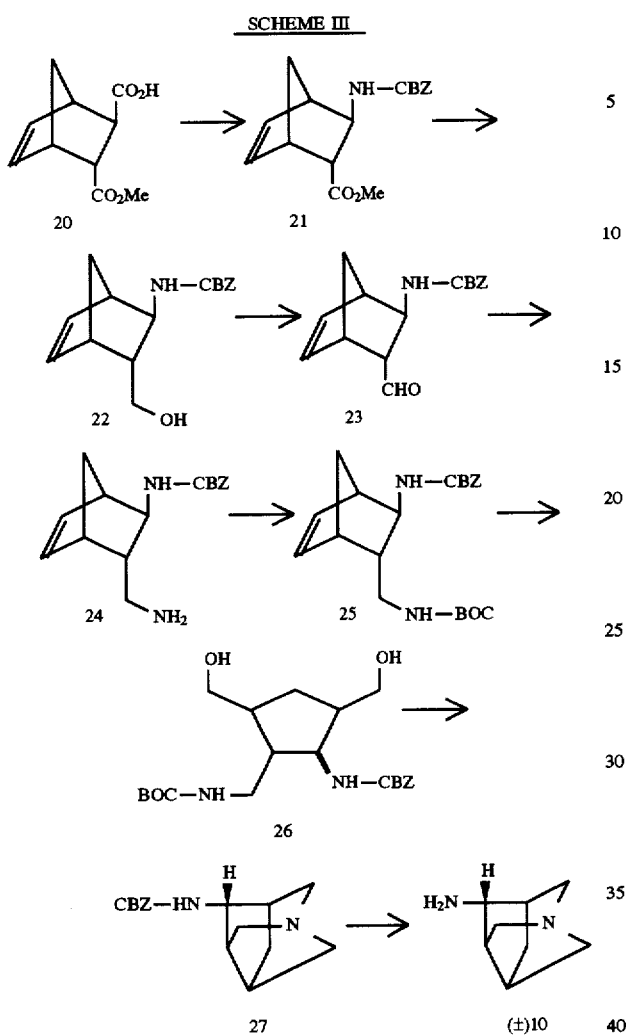

SCHEME IV

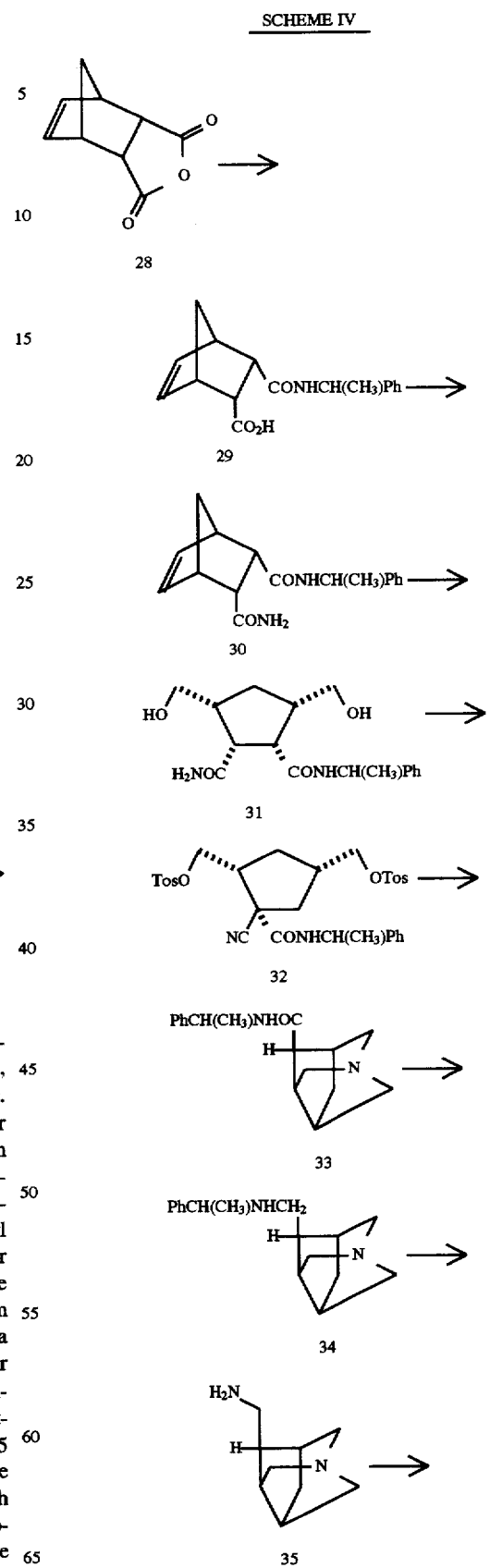

Scheme III describes an alternate preparation of amino-azanoradamantane 10. Treatment of carboxylic acid 20, prepared by the method of Yamamoto [J. Am. Chem. Soc. 1992, V114, 1089] sequentially with ethyl chloroformate or other conventional acid activating reagents and sodium azide gives the acyl azide which is rearranged to the isocyanate by heating under reflux in benzene. Subsequent treatment of the isocyanate with an alcohol, preferably benzyl alcohol in benzene or other suitable inert solvent under reflux gives the benzyl carbamate 21. Reduction of the methyl ester of 21 with a reducing agent such as lithium borohydride gives the alcohol 22 which is oxidized with a Moffat, Swern or chromium based oxidant, (i.e., sulfur trioxide-pyridine) to give the aldehyde 23. Reductive amination gives the amine 24 which is protected as the tert-butylcarbamate 25. Ozonolysis of the tert-butylcarbamate 25 with a reductive workup employing sodium borohydride gives the diol 26. Sequential treatment of the diol 26 with p-toluenesulfonyl chloride, trifluoroacetic acid, and diisopropylethylamine gives the azanoradamantane derivative 27. Removal of the benzyl carbamate with palladium on carbon yields the racemic aminoazanoradamantane 10.

-continued
SCHEME IV

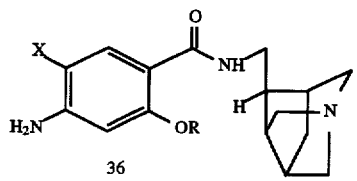

36

Scheme IV describes the preparation of the epimeric aminomethyl-azanoradamantane benzamide 36. Treatment of cis-5-norbornene-endo-2,3-dicarboxylic anhydride 28 (commercially available from Aldrich) with either enantiomer of alpha-methylbenzylamine gives the amide 29 which can be purified to a pure diastereomer by recrystallization or chromatography. Sequential treatment of 29 with CDI and ammonia gives the primary amide 30. Ozonolysis of 30 followed by a reductive workup with sodium borohydride gives the diol 31. Treatment of 31 with an excess of p-toluenesulfonyl chloride in pyridine gives the di-tosylate nitrile 32 which is directly reduced with hydrogen and palladium on carbon to yield the azanoradamantane 33. Reduction of the amide with borane in THF gives the benzyl amine 34 which is then debenzylated with Pearlman's catalyst to give the aminomethyl azanoradamantane 35. Reaction of 35 with 4-amino-5-halo-2-alkoxybenzoic acid in the presence of CDI gives the benzamide 36.

The following non-limiting examples describe and illustrate methods for carrying out the process of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes described in these examples can be used to perform the process of the present invention.

Unless otherwise indicated all starting materials and equipment employed were commercially available.

EXAMPLE A

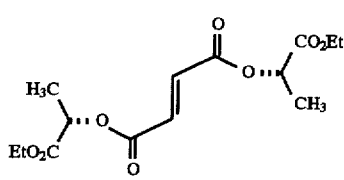

Fumaryl chloride (100 g; 0.653 moles) and ethyl (S)-lactate (147 ml, 1.3 moles) were dissolved in 1.6 liters of toluene with 400 mg of hydroquinone. The reaction mixture was heated between 80° to 85° C. for 18 hours, sweeping the HCl from the mixture with a gentle stream of nitrogen.

The reaction mixture was cooled to –25° C. A second portion of ethyl (S)-lactate (147 ml, 1.3 moles) was added. Triethylamine (Et₃N) (191 ml; 1.37 moles) was added to the reaction mixture, keeping the temperature below –10° C. The reaction mixture was stirred for one hour, allowing the reaction mixture to warm to room temperature. The reaction mixture was washed successively: 2×200 ml 2N HCl, 200 ml water, 4×200 ml 2N NaOH, then 3×250 ml brine. The organic layer was dried over MgSO₄ and concentrated. The residue was diluted to 1.0 liter with 15% EtOAc/hexane and placed on 600 g of silica. The product was eluted with 15% EtOAc/hexane to yield 186 g (90.3%) of A as an oil, which was used without further purification.

NMR (CDCl₃) 1H ppm: 1.3 (6H, t, J=12); 1.57 (6H, d, J=11); 4.22 (4H, q, J=12); 5.19 (2H, q, J=11); 7.0 (2H, s).

EXAMPLE B

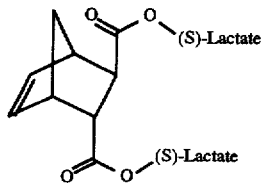

Di-(ethyl (S)-lactate) fumarate A (352 g; 1.112 moles) was dissolved in 5.5 liters of Et₃N and cooled to 0° C. Cyclopentadiene (140 ml; 1.71 moles) was added within ten minutes. The temperature reached 8° C. before lowering to 0° C. The reaction mixture was allowed to warm to room temperature and stirred for 18 hours. The reaction mixture was concentrated to 450.7 g of B as an oil and used without further purification.

The ratio of the two diasteriomers were monitored by HPLC: Supelco LC-18 DB; 65/35 MeCN/H₂O; (2R,3R)/(2S,3S)=92.8/7.2.

EXAMPLE C

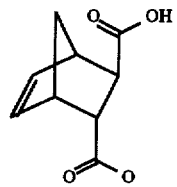

The saponification of diester B to give the chiral diacid C was carried out as described by Helmchen [Modern Synthetic Methods (1986) 261].

EXAMPLE D

[(+)-hexahydro-6β-iodo-2-oxo-3αR,5α-methano-2H-3aβ,6aβ-cyclopenta[b]furan-7S*,-carboxylic acid

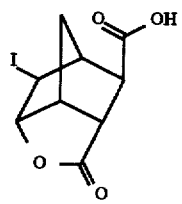

Helmchen's procedure [Modern Synthetic Methods (1986) 261] for the conversion of the olefinic acid intermediate C. to the iodolactone 1 was followed with one modification: The crude iodolactone was not extracted into CH₂Cl₂. The mixture containing the crude iodolactone was stirred for 18 hours. The solid was filtered, dissolved in THF/EtOAc and the workup as described continued. Crude lactate ester (471.5 g; 1.17 mole) from Example B was converted to 227.5 g (63%) of the iodolactone 1.

$C_9H_9IO_4$ MW 308.06 Calc: C, 35.09; H, 2.94; I, 41.19 Found: C, 35.28; H, 2.92; I, 41.23
[a]hd D=+54.4° (c=1.0 in EtOH)

EXAMPLE 1

(+)-Hexahydro-6β-iodo-2-oxo-3αR,5α-methano-2H-3aβ,6aβ-cyclopenta[b]furan-7S-carboxamide

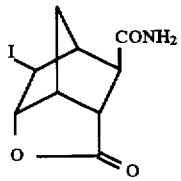

Iodolactone 1 (227.5 g; 0.73 mol) was suspended in $SOCl_2$ (132 mL) and gently warmed to reflux, whereupon complete dissolution occurred. The reaction mixture was concentrated to remove the excess $SOCl_2$. The residue was dissolved in toluene (350 ml) and slowly added to a mixture of liquid $NH_3$ (85 ml) and 2.0 liters of THF cooled to –30° C. The reaction mixture was stirred for 0.5 hour before adding 500 ml of $H_2O$. The layers were separated and the organic layer was washed with brine (500 ml), dried over $MgSO_4$ and concentrated to an oil. The oil slowly crystallized when triturated with EtOAc. The solid was filtered and washed with EtOAc and dried in vacuum, to yield 181.5 g (81%) of compound 2 as a white solid.

$C_9H_{10}INO_3$ MW 307.08 Calc: C, 35.20; H, 3.28; N, 4.56; I, 41.32 Found: C, 35.40; H, 3.26; N, 4.50; I, 41.20
$[a]_D$=+34.5° (C=1.0 in EtOH)

EXAMPLE 2

(+)-Hexahydyro-6β-iodo-2-oxo-3αR,5α-methano-2H-3αβ,6αβ-cyclopenta[b]furan-7S-amine, 4-methylbenzenesulfonate

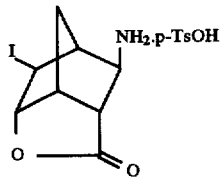

Compound 2 (30.0 g; 0.096 mol) was dissolved in $CH_3CN$ (500 ml). HTIB [hydroxy(tosyloxy) iodobenzene; 42 g; 0.108 mol] was added to the reaction mixture and stirring was continued. The mixture became a thick mass within 5 minutes. The mixture was slowly warmed to reflux where the solid mass became stirrable again. The reaction mixture was allowed to cool to 35° C. IBDA (iodobenzene diacetate; 15.4 g; 0.048 mol) was added and the mixture thickened again. The mixture was reheated to 65° C. where the solid mass became stirrable again. The reaction mixture was stirred 18 hours, filtered, washed with $CH_3CN$ and suction dried to yield 35.4 g (82%) of intermediate 3.

$C_{15}H_{18}INSO_5$ MW 451.26 Calc: C, 39.92; H, 4.02; N, 3.20; S, 7.11 Found: C, 39.96; H, 4.04; N, 2.90; S, 7.38
$[a]_D$=+30.0° (c=1.0 in EtOH)

EXAMPLE 3

(–)-N-(3aβ,6aβ-hexahydro-6β-iodo-2-oxo-3αR,5α-methano-2H-cyclopenta[b]furan-7S-yl)-4-methylbenzenesulfonamide

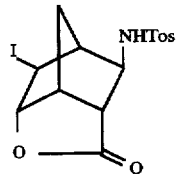

The tosylate salt 3 (1.0 g; 0.0022 mol) was dissolved in pyridine (5.0 ml). p-Toluenesulfonyl chloride (476 mg; 0.0025 mol) was added and the reaction mixture stirred for 2 hours and concentrated. The residue was partitioned between THF/brine. The organic layer was washed with dilute HCl then with dilute $K_2CO_3$, and dried over $MgSO_4$, and concentrated. The residue was placed on 50 g of silica and eluted with 50 mL of 50% EtOAc/heptane. The solution was concentrated to an oil which slowly crystallized to yield 913 mg (95%) of compound 4.

$C_{15}H_{16}INSO_4$ MW 433.25 Calc: C, 41.58; H, 3.72; N, 3.23; S, 7.40 Found: C, 41.49; H, 3.79; N, 3.28; S, 7.77
$[a]_D$=–65.6° (c=1.0 in EtOH)

EXAMPLE 4

(–)-3R-[[(4-methylphenyl) sulfonyl]amino]-bicyclo-[2.2.1]hept-5-ene-2αR-carboxylyic acid

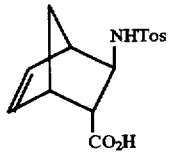

Compound 4 (27.0 g; 0.062 mole) and $Zn°$ (16.2 g; 0.249 mol) were combined in HOAc (100 ml) and heated to reflux for one half hour. The reaction mixture was cooled and filtered through Celite®. The filtrate was concentrated and the residue suspended in $H_2O$, whereupon the oil crystallized. The solid was filtered, washed with $H_2O$ and suction dried to yield 18.4 g (96.8%) of Compound 5 as a white solid.

$C_{15}H_{17}NSO_4$ MW 307.37 Calc: C, 56.95; H, 5.73; N, 4.43; S, 10.14 Found: C, 57.08; H, 5.42; N, 4.36; S, 10.33
$[a]_D$=–24.9° (c=1.0 in EtOH)

EXAMPLE 5

N-(5αS-hydroxyethyl-3-oxo-3aα,6aα-cyclopenta[c]furan-4βR-yl)-4-methylbenzenesulfonamide

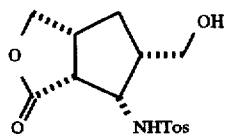

Ozone was bubbled through a solution of carboxylic acid 5 (2.0 g, 6.5 mmol) in ethyl acetate/methanol (24 mL; 5:1)

at −78° C. until a light blue color persisted. After stirring for an additional 0.5 hour at −78° C., argon was bubbled through the solution for 25 minutes to remove excess ozone. To the colorless solution was then added sodium borohydride pellets (1.07 g, 32.5 mmol) at −78° C. The reaction mixture was allowed to warm to room temperature and stirred for 40 hours. To the reaction mixture was added 3 drops of methyl orange/methanol indicator followed by a solution of 2N HCl/methanol to give a light pink color and the reaction was then stirred for 72 hours at room temperature. The mixture was concentrated in vacuo. To the residue was added brine (35 mL) and the mixture was extracted with ethyl acetate (3×50 mL). The combined extracts were washed successively with water and brine, dried over $MgSO_4$, filtered and concentrated to give the title compound 6 as a waxy white solid (2.01 g, 100%).

$^1$H NMR ($CD_3OD$): 1.25 (1H, m); 2.09 (2H, m); 2.40 (3H, s); 2.78 (2H, distorted d); 2.97 (1H, m), 3.36 (1H, d of d), 3.50 (1H, d of d), 3.68 (1H, d of d); 4.06 (1H, d); 4.27 (1H, d of d); 7.34 (2H, d); 7.82 (2H, d).

CMR ($CD_3OD$): $^{13}$C. (ppm): 19.69, 32.16, 38.88, 38.89, 50.99, 51.11, 57.79, 60.80, 70.79, 126.59, 128.81, 142.84, 178.36.

EXAMPLE 6

(+)-1α,4α-bis(hydroxymethyl)-3β-[[4-methylphenyl)sulfonyl]amino]cyclopentane-2α-carboxamide

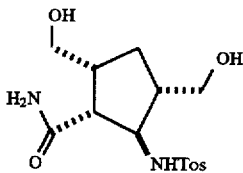

A solution of lactone 6 (2.0 g, 6.5 mmol) in methanol (50 mL) in a Parr Shaker was pressurized with ammonia gas to 50 psi for 4 hours at 60° C. The solution was then filtered through Celite and concentrated in vacuo to give a white solid. The solid was recrystallized from ethanol to give primary amide 7 (1.52 g, 72%).

Analysis for $C_{15}H_{22}N_2SO_5$*0.5 $H_2O$: Calc: C, 51.27; H, 6.60; N, 7.97 Found: C, 51.16; H, 6.53; N, 7.96
$[a]_D$=+46.8° (c=1.10 in $CH_3OH$)

EXAMPLE 7

(+)-1,1-dimethylethyl-N-[[1α,4α-bis(hydroxymethyl)-3β-[[(4-methylphenyl)sulfonyl]amino]-cyclopentan-2α-yl]methyl]carbamate

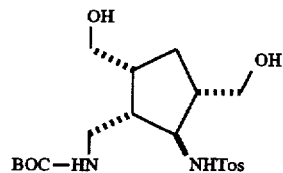

To a suspension of amide 7 (1.0 g, 2.9 mmol) in THF 100 ml) was added dropwise a 1M solution of borane-THF (20.4 mL, 20.4 mmol) over 20 minutes. The reaction mixture was stirred for 1 hour at room temperature followed by heating to reflux for 18 hours. The reaction mixture was cooled to 0° C. and 15% aqueous HCl (100 mL) was added. The reaction was then allowed to warm to room temperature while stirring for 14 hours. The solution was then concentrated in vacuo to a white foam which was dissolved in water (10 mL) and then treated with 1N NaOH (10 mL). The solution was stirred for 3 hours, saturated with NaCl, and extracted with THF. The combined extracts were dried over $MgSO_4$ and then concentrated in vacuo to give oil. The oil was passed through a pad of silica eluting with ethyl acetate followed by 20% $CH_3OH(NH_3)$/THF to give the free amine (700 mg, 74%). To a solution of the amine (570 mg, 1.73 mmol) and triethylamine (0.45 mL, 1.9 mmol) in acetone/water (10 ml) was added BOC-ON (2-(tert-butoxy-carbonyloxyimino)2-phenylacetonitrile; 470 mg, 2.9 mmol) and the reaction stirred for 18 hours at room temperature. The solution was extracted with ethyl acetate (3X). The combined extracts were washed successively with water and brine, dried over $MgSO_4$, filtered, and concentrated in vacuo to an oil. The oil was passed through a pad of silica gel eluting with ethyl acetate to give the title compound 8 (740 mg, 100%).

Analysis for $C_{20}H_{32}N_2SO_6$. ½ $H_2O$ Calc: C, 54.90; H, 7.60; N, 6.40 Found: C, 54.91; H, 7.47; N, 6.07

$[e]_D$=+22.4° (c=0.157 in chloroform)

EXAMPLE 8

(−)-N-(hexahydro-2,5β-methano-1H-3aS,3aα,6aα-cyclopenta[c]pyrrol-4α-yl)-4-methylbenzenesulfonamide

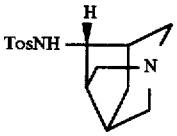

To a solution of diol 8 (207 mg, 0.484 mmol) in dry pyridine (2.4 mL) at −20° C. was added p-toluenesulfonyl chloride (369 mg, 1.94 mmol) with stirring. After dissolution was complete the solution was allowed to stand at 0° C. for 21 hours. The reaction mixture was poured onto ice and extracted with ethyl acetate (3X). The combined extracts were washed successively with water (5X) and brine and then dried over sodium sulfate. Concentration gave a colorless foam (357 mg). The foam was dissolved in trifluoroacetic acid (5 mL) and allowed to stand for 15 minutes at room temperature after which time the reaction mixture was concentrated under vacuum. The resulting residue was dissolved in acetonitrile (10 mL) and treated with diisopropylethylamine (433 mg, 3.35 mmol). After 4 days at room temperature the pale yellow solution was warmed to 46° C. for 2 hours. Concentration gave a residue which was treated with 4N KOH/presaturated with NaCl (5 mL) and extracted with chloroform (5X). The combined extracts were washed with water (2X) and brine and dried over sodium sulfate. Concentration produced a residue which was dissolved in chloroform (5 mL) and filtered through Celite. Concentration gave the title compound 9 (134 mg, 96%) as a pale yellow solid: mp 203°–205° C.

Analysis for $C_{15}H_{20}N_2SO_2$: Calc: C, 61.62; H, 6.89; N, 9.58; S, 10.97 Found: C, 61.31; H, 6.91; N, 9.30; S, 10.80
$[a]_D$=3.0° (c=0.76 in $CHCl_3$).

EXAMPLE 9

Hexahydro-2,5β-methano-1H-3αS,3aα,6aα-cyclopenta[c]pyrrol-4α-amine

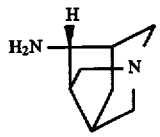

To liquid ammonia (30mL) at −33° C. was added a solution of tosylamide 9 (539 mg, 1.84 mmol) in THF (7 mL). Calcium metal (319 mg, 7.96 mmol) was added in three portions over 5 minutes. After 30 minutes the dark blue reaction was quenched with addition of solid ammonium chloride (985 mg, 18.4 mmol). Concentration gave a residue which was treated with 4N KOH-presaturated with NaCl (9.2 mL). The suspension was filtered through Celite and the solid was washed with THF. The filtrate was extracted with THF (7X) and the combined THF rinses and extracts were dried over sodium sulfate. Concentration gave the title compound 10 (0.29 g) as a colorless waxy solid.

EXAMPLE 10

(+)-4-amino-5-chloro-N-(hexahydro-2,5β-methano-1H-3aS,3aα,6aα-cyclopenta[c]pyrrol-4α-yl)-2-methoxybenzamide, monohydrochloride

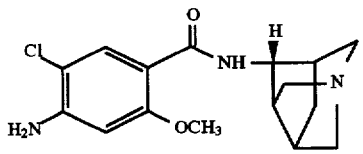

To a solution of 4-amino-5-chloro-2-methoxybenzoic acid (375 mg, 1.86 mmol) in DMF (1.9 mL) was added carbonyldiimidazole (302 mg, 1.86 mmol). After 1 hour at room temperature a solution of the amine 10 (257 mg, 1.86 mmol) in DMF (1.9 mL) was added and the resulting pale yellow solution was stirred at room temperature for 3 days. Concentration gave a yellow solid which was triturated with ethyl acetate (6 mL), filtered, and rinsed with cold (0° C.) ethyl acetate (1.5 mL). The solid was dried in vacuo at 45° C. to give the free base of the title compound 11 as a pale yellow solid (362 mg, 60%). To a solution of free base (343 mg) in 95% ethanol (10 mL) was added ethanolic HCl [prepared from acetyl chloride (75 mg, 1.07 mmol) and 95% ethanol (0.5 mL)]. The solution was allowed to stand at 0° C. for 24 hours and filtration of the resulting crystalline solid and rinsing with cold (0° C.) 95% ethanol (1.5 mL) gave the desired material which was dried at 63° C. in vacuo for 16 hours to afford the title compound 11 (337 mg, 88%) as an almost colorless powder.

Analysis for $C_{16}H_{20}N_3O_2Cl \cdot HCl \cdot H_2O$ Calc: C, 51.07; H, 6.16; N, 11.17; Cl, 18.84 Found: C, 50.80; H, 6.16; N, 11.00; Cl, 18.54

EXAMPLE 11

Methyl 3-[[(phenylmethoxy)carbonyl]amino]-2-bicyclo[2.2.1]hept-5-enecarboxylate

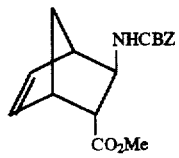

To a solution of carboxylic acid 20 (1.88 g, 9.58 mmol) and triethylamine (1.65 mL, 1.26 g, 12.5 mmol) in acetone (30 mL) at 0° C. was added ethyl chloroformate (0.92 mL, 1.0 g, 9.6 mmol) dropwise over several minutes. After the addition was complete the solution was stirred for 1 hour at 0° C. A solution of sodium azide (1.87 g, 28.7 mmol) in water (30 mL) was added and the reaction mixture was stirred for an additional hour at 0° C. The solution was poured into ice water and the resulting mixture was extracted with ethyl acetate (4×50 mL). The combined organic extracts were washed sequentially with sodium bicarbonate and brine and then dried over sodium sulfate. Concentration gave a residue which was dissolved in dry benzene (50 mL) and heated under reflux for 1.5 hours. Benzyl alcohol (2.07 g, 19 mmol) was added and heating under reflux was continued for an additional 2.5 hours. Concentration gave a pale yellow oil which was crystallized from $Et_2O$/hexane to give the title compound 21 (2.1 g, 73%) as colorless crystals: mp 73°–76° C.

Analysis calculated for $C_{17}H_{19}NO_4$ C, 67.76; H, 6.36; N, 4.65 Found: C, 67.59; H, 6.46; N, 4.63

EXAMPLE 12

Phenylmethyl N-[3-hydroxymethyl)bicyclo[2.2.1]hept-5-en-2-yl]carbamate

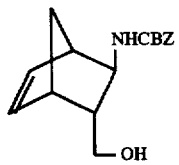

To a solution of methyl ester 21(111 mg, 0.37 mmol) in dry THF (1 mL) and absolute methanol (0.031 mL, 0.76 mmol) was added a solution of lithium borohydride (0.37 mL of a 2M solution in THF, 0.76 mmol) and the solution was stirred for 2 hours at room temperature before quenching with 1N HCl (3 mL). The resulting mixture was extracted with ethyl acetate (3×15 mL) and the combined extracts were washed sequentially with sodium bicarbonate, water and brine, and dried over sodium sulfate. Concentration gave a colorless oil which was purified by chromatography on silica gel eluting with 50/50 ethyl acetate/hexane to give the title compound 22 (84 mg, 84%) as a colorless oil which crystallized on standing: mp 111°–113° C.

Analysis Calculated for $C_{16}H_{19}NO_3 \cdot 0.15 \, H_2O$ C, 69.62; H, 7.05; N, 5.07. Found: C, 69.81; H, 7.05; N, 5.07.

EXAMPLE 13

Phenylmethyl N-(3-formylbicyclo[2.2.1]hept-5-en-2-yl)carbamate

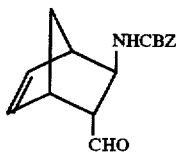

To a solution of alcohol 22 (404 mg, 1.48 mmol) and triethylamine (450 mg, 4.44 mmol) in dry DMSO (5 mL) was added sulfur trioxide-pyridine complex (706 mg, 4.44 mmol). The pale yellow solution was stirred at room temperature for 15 minutes, then poured into ice water (50 mL). The mixture was extracted with ethyl acetate (3×50 mL) and the combined organic extracts were washed successively with water (4×30 mL) and brine and dried over sodium sulfate. Concentration gave the title compound 23 (380 mg, 95%) as a colorless solid: mp 75°–79° C.

Analysis calculated for $C_{16}H_{17}NO_3 \cdot 0.2\ H_2O$ C, 69.90; H, 6.38; N, 5.10. Found: C, 70.05; H, 6.68; N, 5.08.

EXAMPLE 14

Phenylmethyl N-[3-(aminomethyl)bicyclo[2.2.1]hept-5-en-2-yl]carbamate

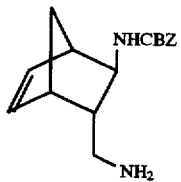

To a solution of the aldehyde 23 (243 mg, 0.89 mmol) in methanol (9 mL) at room temperature was added ammonium acetate (690 mg, 8.9 mmol) followed by borane-pyridine (83 mg, 0.89 mmol). After stirring for 2.5 hours at room temperature the solution was concentrated in vacuo to give a residue which was treated with 20% aqueous potassium carbonate (15 mL) and extracted with chloroform (3×15 mL). The combined extracts were washed with water and brine and dried over sodium sulfate. Concentration gave a residue which was chromatographed on silica gel eluting with 4/96 EtOH(NH$_3$)/ethyl acetate to give the title compound 24 (30 mg, 12%) as a colorless glass.

$^1$H NMR (300 MHz, CDCl$_3$) δ 7.42–7.27 (5H, m), 6.16 (1H, m), 6.10 (1H, dd, J=5.3 Hz), 5.09 (2H, s), 5.05 (1H, br d, J=3 Hz), 3.12 (1 H, br d, J=5 Hz), 2.82 (1H, br s), 2.74 (1H, br s), 2.65 (1H, dd, J=12, 7 Hz), 2.52 (1H, dd, J=12, 7 Hz), 1.73–1.64 (1H, m), 1.63 (1H, dd, J=9, 1 Hz), 1.50 (1H, d, J=9 Hz), 1.39 (2H, s).

EXAMPLE 15

1,1-Dimethylethyl N-[3-[[(phenylmethoxy)carbonyl]-amino]bicyclo[2.2.1]hept-5-en-2-yl]methylcarbamate

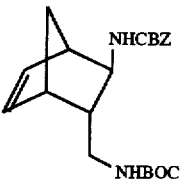

To a solution of the amine 24 (30 mg, 0.11 mmol) in dry THF (3 mL) was added di-tert-butyldicarbonate (28 mg, 0.13 mmol). After stirring for 24 hours at room temperature the solution was concentrated in vacuo to give a residue which was chromatographed on silica gel eluting with 30/70 ethyl acetate/hexane to give the title compound 25 (36 mg, 88%) as a colorless oil.

MS M+1 calculated for $C_{21}H_{28}N_2O_4$ 373 Found: 373. $^1$H NMR (300 MHz, CDCl$_3$) δ 7.40–7.28 (5H, m), 6.15 (2H, m), 5.50 (1H, br s), 5.10 (2H, s), 4.89 (1H, d, J=5 Hz), 3.24–3.07 (2H, m), 2.79 (2H, br s), 2.74 (1H, s), 1.86 (1H, br s), 1.63 (1H, d, J=9 Hz), 1.51 (1H, d, J =9 Hz), 1.44 (9H, s). $^{13}$C NMR (75 MHz, CDCl$_3$) δ 156.2, 156.1, 136.3, 136.0, 135.3, 128.5, 128.1, 66.8, 56.0, 50.1, 49.9, 48.8, 46.8, 44.2, 44.0, 28.3.

EXAMPLE 16

1,1-Dimethylethyl N-[1,4-bis(hydroxymethyl)-3-[[(phenylmethoxy)carbonyl]amino]cyclopentan-2-yl]carbamate

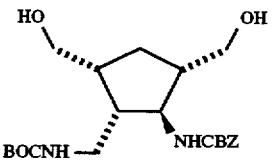

Ozone was bubbled through a solution of BOC-amine 25 (36 mg, 0.097 mmol) in 5:1 CH$_2$Cl$_2$/MeOH at −78° C. until a blue color persisted (3 minutes). Argon was bubbled through the solution until the blue color disappeared. Sodium borohydride (18 mg, 0.48 mmol) was added to the solution at −78° C. and the reaction mixture was allowed to warm up to room temperature over 1 hour. After stirring for an additional 16 hours at room temperature, brine (10 mL) was added and the reaction mixture was extracted with methylene chloride (4×10 mL). The combined organic extracts were washed successively with water and brine and dried over sodium sulfate. Concentration gave a colorless oil which was purified by preparative thin-layer chromatography on silica gel eluting (2X) with 4/96 EtOH/ethyl acetate to give the title compound 26 (11 mg, 27%) as colorless crystals: mp 142°–144° C.

MS M+1 calculated for $C_{21}H_{32}N_2O_6$ 409.2339 Found: 409.2364 Analysis calculated for: $C_{21}H_{32}N_2O_6 \cdot 0.25H_2O$ C,61.07; H, 7.93; N, 6.78 Found: C, 61.02; H, 7.67; N, 6.73

EXAMPLE 17

Phenylmethyl N-(hexahydro-2,5β-methano-1H-3aα, 6aα-cyclopenta[c]pyrrol-4α-yl)carbamate

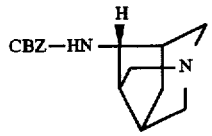

To a solution of diol 26 (18 mg, 0.044 mmol) in pyridine (0.6 mL) at 0° C. was added solid p-toluenesulfonyl chloride (45 mg, 0.24 mmol) with stirring. After dissolution was complete the solution was allowed to stand at 0° C. for 23 hours. The solution was poured onto ice (15 g) and extracted with ethyl acetate (3×10 mL). The combined organic extracts were washed successively with water (3×30 mL) and brine (30 mL) and dried over sodium sulfate. Concentration gave the di-tosylate (23 mg) as a colorless oil which was treated directly with freshly-distilled trifluoroacetic acid (0.5 mL) at room temperature. After stirring for 15 minutes the solution was concentrated in vacuo to give a residue which was dissolved in acetonitrile (1 mL) and treated with diisopropylethylamine (31 mg, 0.24 mmol). After 21 hours at room temperature the solution was concentrated in vacuo to give a residue which was treated with aqueous 15% potassium carbonate (1 mL) and extracted with chloroform (3×15 mL). The combined organic extracts were washed successively with water and brine and dried over sodium sulfate. Concentration gave the title compound 27 (9.2 mg, 78%) as colorless crystals.

MS calculated for $C_{16}H_{20}N_2O_2$: 272.1525 Found: 272.1524

EXAMPLE 18

2,5β-methano-1H-3aα, 6aα-cyclopenta[c]-pyrrol 4-amine

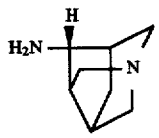

To a suspension of 10% palladium on carbon (2 mg) in methanol (0.4 mL) was added a solution of benzyl carbamate 27 (9.2 mg) in methanol (0.4 mL) at room temperature. The suspension was stirred under an atmosphere of hydrogen (1 atm) for 1 hour. Removal of the catalyst by filtration and concentration of the filtrate gave the title compound (±)10 (4.2 mg, 89%) as a waxy semisolid which was used directly without further purification.

EXAMPLE 19

3-[[(1-Phenylethyl)amino]carbonyl]-2-bicyclo-[2.2.1]hept-5-enecarboxylic acid

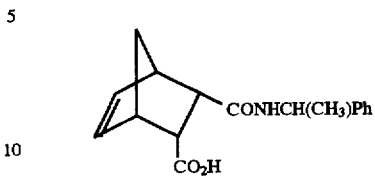

To a solution of cis-5-norbornene-endo-2,3-dicarboxylic anhydride 28 in toluene is added alpha-methylbenzylamine (1 equivalent) and the solution is heated under reflux for 1 hour. After cooling, the solution is concentrated in vacuo to give the title compound 29. Recrystallization affords the enantiomerically pure material, when a single enantiomer of alpha-methylbenzylamine is employed.

EXAMPLE 20

3-[[(1-Phenylethyl)amino]carbonyl]-2-bicyclo-[2.2.1]hept-5-enecarboxamide

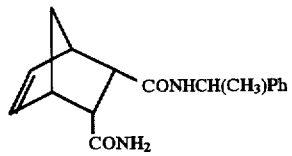

To a solution of the carboxylic acid 29 in freshly distilled DMF is added CDI (1 equivalent). After stirring for 1 hour at room temperature, ammonia gas is bubbled through the solution until the reaction is complete, as judged by disappearance of the acyl imidazolide intermediate on TLC eluting with EtOH/methylene chloride. Concentration affords a residue which is dissolved in chloroform and washed successively with dilute HCl, water, and brine and dried over sodium sulfate. Concentration affords the primary amide 30.

EXAMPLE 21

1,4-Bis(hydroxymethyl)-N-(1-phenylethyl)-2,3-cyclopentane dicarboxamide

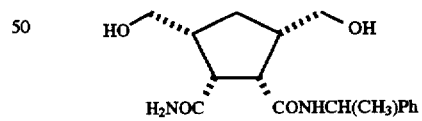

Through a solution of olefin 30 in 5:1 methylene chloride/methanol at −78° C. is bubbled ozone until the olefin 30 is consumed by TLC. After 5 minutes at −78° C., solid sodium borohydride (3 equivalents) is added and the reaction is allowed to warm to room temperature over 1 hour. After stirring at room temperature for an additional 16 hours, brine is added and the mixture is extracted with ethyl acetate (3X). The combined organic extracts are washed successively with water and brine and dried over sodium sulfate. Concentration gives a residue which is chromatographed on silica gel eluting with EtOH/methylene chloride to afford the title compound 31.

EXAMPLE 22

1,4-Bis [[[(4-methylphenyl) sulfonyl]oxy]methyl]-3-cyano-N-(1-phenylethyl)-2-cyclopentanecarboxamide

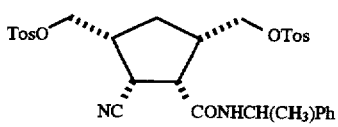

To a solution of diol 31 in pyridine at 0° C. is added p-toluenesulfonyl chloride (5 equivalents). After allowing the solution to stand for 16 hours at 0° C. the solution is poured onto ice and extracted with ethyl acetate (3X). The combined organic extracts are washed successively with water and brine and dried over sodium sulfate. Concentration gives the title compound 32 which is used without further purification.

EXAMPLE 23

Hexahydro-N-(1-phenylethyl)-2,5β-methano-1H-3aα,6aα-cyclopenta[c]pyrrole-4-carboxamide

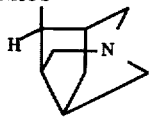

To a suspension of palladium on carbon in ethanol is added diisopropylethylamine (5 equivalents) followed by a solution of the ditosylate nitrile 32 in ethanol. The suspension is stirred under an atmosphere of hydrogen for 16 hours at room temperature. Removal of the catalyst by filtration and concentration of the filtrate in vacuo gives a residue which is treated with 15% potassium carbonate and extracted with chloroform (3X). The combined organic extracts are washed successively with water and brine and dried over sodium sulfate. Concentration gives a residue which is chromatographed on silica gel eluting with ammonia-saturated methanol/chloroform to give the title compound 33.

EXAMPLE 24

Hexahydro-N-(1-phenylethyl)-2,5β-methano-1H-3aα,6aα-cyclopenta[c]pyrrole-4-methanamine

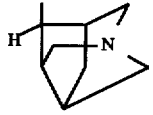

To a solution of amide 33 in THF is added borane-tetrahydrofuran (5 equivalents) and the reaction mixture is heated under reflux for 3 hours. Concentration gives a residue which is treated with concentrated aqueous HCl. The aqueous solution is basified with KOH, saturated with solid sodium chloride, and extracted with chloroform (3X). The combined organic extracts are washed successively with water and brine and dried over sodium sulfate. Concentration gives a residue which is chromatographed on silica gel eluting with MeOH(NH₃)/chloroform to give the title compound 34.

EXAMPLE 25

Hexahydro-2,5β-methano-1H-3aα,6aα-cyclopenta[c]pyrrole-4-methanamine

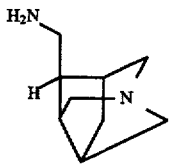

A solution of benzylamine 34 in ethanol is added to a Pd(OH)₂ in ethanol and pressurized with hydrogen and heated at 60° C. until the benzylamine is consumed. The reaction mixture is filtered and concentrated in vacuo to give the aminomethyl azanoradamantane 35 which is used directly without further purification.

EXAMPLE 26

(+)-4-Amino-5-chloro-N-(hexahydro-2,5β-methano-1H-3aα,6aα-cyclopenta[c]pyrrol-4α-yl)-2-methoxybenzamide

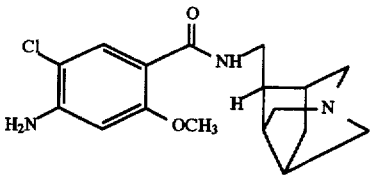

To a solution of 4-amino-5-chloro-2-methoxybenzoic acid in freshly distilled DMF is added CDI (1 equivalent). After 1 hour at room temperature a solution of amine 35 (1 equivalent) in DMF is added. The reaction mixture is stirred at room temperature for 16 hours and concentrated in vacuo to give a residue which is treated with 15% potassium carbonate and extracted with chloroform (3X). The combined organic extracts are washed successively with water and brine and then dried over sodium sulfate. Concentration gives a solid which is purified on silica gel eluting with 7/93 MeOH(NH₃)/chloroform to give the title compound 36as a colorless solid.

What is claimed is:

1. A process for the preparation of a γ-lactone of the formula,

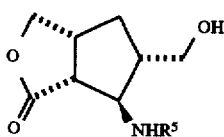

comprising:

(a) oxidatively cleaving a compound of the formula

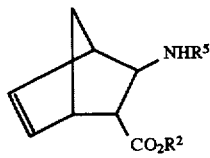

wherein R⁵ is selected from the group consisting of tosyl, pivaloyl and trityl. R² is selected from the group consisting of H, a metal cation, alkyl, and a chiral auxiliary group; and b) sequentially reducing the compound produced in step (a) and subjecting to acid induced lactonization to produce the γ-lactone of the formula

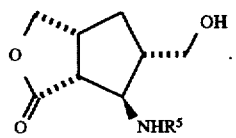

2. The process of claim 1 wherein the compound of the formula

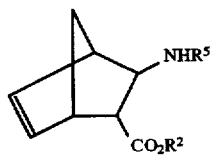

is oxidatively cleaved by ozone; and (b) subsequently reduced to produce the γ-lactone of the formula

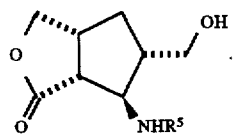

3. The process according to claim 1 further comprising sequentially subjecting the γ-lactone to ammonolysis to produce a primary amide diol of the formula

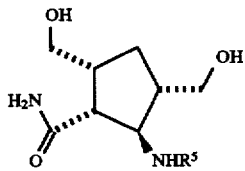

subjecting said primary amide diol to amide reduction to produce a primary amine of the formula

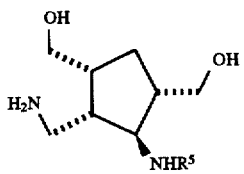

subjecting said primary amine to amine protection to produce a protected amine of the formula

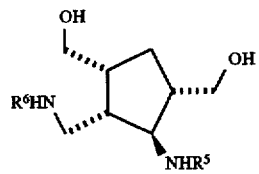

wherein R⁶ is a protecting group;

subjecting said protected amine to diol bis-tosylation and amine deprotection to produce an azanoradamantane of the formula

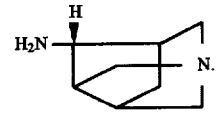

4. The process of claim 3 further comprising coupling the azanoradamantane with a 4-amino-5-halo-2-alkoxybenzoic acid to produce a compound of the formula

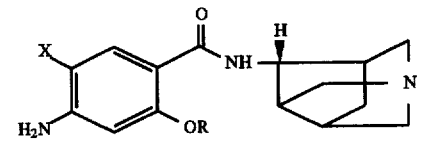

wherein X is halogen and R is alkyl.

5. A process for preparing an azanoradamantane comprising:

reacting an iodolactone of the formula

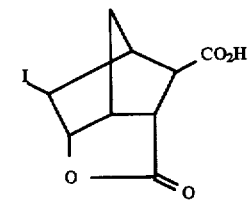

with thionyl chloride and treating with ammonia to yield a primary amide of the formula

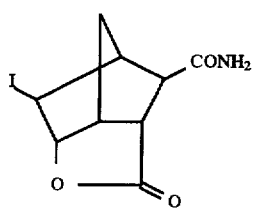

treating the primary amide with hydroxy (tosyloxy) iodobenzene to yield a p-toluenesulfonic acid salt of the formula

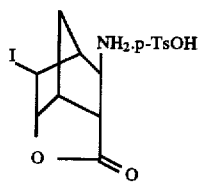

tosylating the p-toluenesulfonic acid salt with toluenesulfonyl chloride in pyridine to yield a tosylamine of the formula

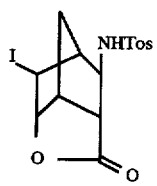

treating the tosylamine with zinc in acetic acid to yield a norbornene carboxylic acid of the formula

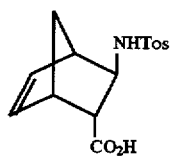

treating the norbornene carboxylic acid sequentially with ozone and with sodium borohydride and an acidic workup to yield a gamma-lactone of the formula

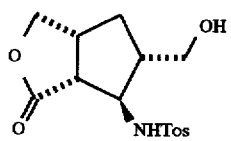

performing ammonolysis of the gamma-lactone to afford a primary amide diol of the formula

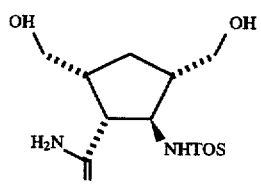

reducing and protecting the amine with BOC to produce a tert-butyl carbamate diol of the formula

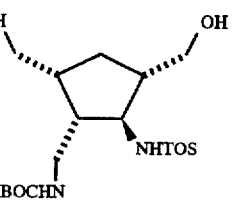

and sequentially treating the tert-butyl carbamate diol with toluenesulfonyl chloride, trifluoroacetic acid and diisopropylethylamine to produce a tosylamine azanoradamantane of the formula

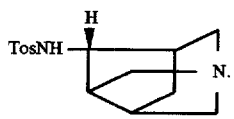

6. The process of claim 5 further comprising the removal of the tosylate from the tosylamine azanoradamantane to produce an aminoazanoradamantane of the formula

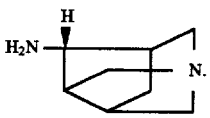

7. The process of claim 1 wherein the reduction is achieved with sodium borohydride.

8. The process of claim 3 wherein the oxidative cleavage is achieved by ozonolysis.

9. The process of claim 3 wherein the reducing is achieved by sodium borohydride.

10. The process of claim 4 wherein the 4-amino-5-halo-2-alkoxybenzoic acid is 4-amino-5-chloro-2-methoxybenzoic acid.

11. The process of claim 1 wherein the compound

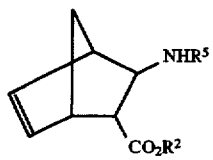

is prepared by treating

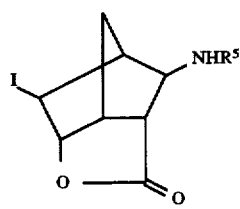

with zinc in acetic acid.

12. The process of claim 6 further comprising the step of coupling the aminoazanoradamantane with a 4-amino-5-halo-2-alkoxybenzoic acid derivative in the presence of 1,1'-carbonyldiimidazole to produce a compound of the formula

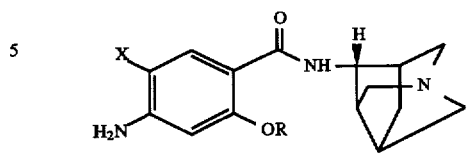

wherein X is halogen and R is alkyl.

13. The process of claim 12 wherein the 4-amino-5-halo-2-alkoxybenzoic acid is 4-amino-5-chloro-2-methoxy benzoic acid.

* * * * *